United States Patent [19]

Iba

[11] Patent Number: 5,582,330
[45] Date of Patent: Dec. 10, 1996

[54] SPECIFIC VOLUME DISPENSER

[75] Inventor: Wayne S. Iba, Mission Viejo, Calif.

[73] Assignee: Allergan, Inc., Irvine, Calif.

[21] Appl. No.: 365,571

[22] Filed: Dec. 28, 1994

[51] Int. Cl.$^6$ ............................................. B65D 37/00
[52] U.S. Cl. ......................... 222/212; 222/215; 604/212
[58] Field of Search ................................. 222/209, 212, 222/215, 563, 564, 420; 401/185, 186; 604/212; 73/864.11

[56] References Cited

U.S. PATENT DOCUMENTS

| | | | |
|---|---|---|---|
| 29,699 | 8/1860 | Isaacen | 222/189 |
| D. 327,008 | 6/1992 | Friedman | D9/521 |
| 2,317,002 | 4/1943 | Ulvick | 401/186 |
| 2,729,505 | 1/1956 | Harvey | 239/327 |
| 2,738,107 | 3/1956 | Graham | 222/211 |
| 2,768,623 | 10/1956 | Marchand | 604/204 |
| 2,864,367 | 12/1958 | Mende | 222/215 |
| 3,295,523 | 1/1967 | Weichselbaum | 604/217 |
| 3,366,284 | 1/1968 | Marona et al. | 222/215 |
| 3,506,162 | 4/1970 | Schwartzman | 222/207 |
| 4,020,979 | 5/1977 | Shay | 222/211 |
| 4,044,836 | 8/1977 | Martin et al. | 169/30 |
| 4,111,200 | 9/1978 | Sbarra et al. | 128/233 |
| 4,131,217 | 12/1978 | Sandegren | 222/82 |
| 4,278,206 | 7/1981 | Prussin | 239/327 |
| 4,282,986 | 8/1981 | Ekenstam et al. | 222/1 |
| 4,349,129 | 9/1982 | Amneus | 222/41 |
| 4,771,769 | 9/1988 | Hegemann et al. | 128/200.22 |
| 4,773,458 | 9/1988 | Touzani | 150/55 |
| 4,821,924 | 4/1989 | Kozam | 222/212 |
| 4,860,738 | 8/1989 | Hegemann et al. | 128/200.22 |
| 4,875,602 | 10/1989 | Chickering et al. | 222/187 |
| 4,921,137 | 5/1990 | Heijenga | 222/107 |
| 4,951,822 | 8/1990 | Fontana et al. | 206/530 |
| 5,052,589 | 10/1991 | O'Meara | 222/83 |
| 5,076,474 | 12/1991 | Hansen | 222/420 |
| 5,116,311 | 5/1992 | Löfstedt | 604/54 |
| 5,121,856 | 6/1992 | Weiler et al. | 222/209 |
| 5,127,553 | 7/1992 | Weinstein | 222/158 |
| 5,195,658 | 3/1993 | Hoshino | 222/92 |
| 5,238,157 | 8/1993 | Gentile | 222/541 |
| 5,261,571 | 11/1993 | Goncalves | 222/214 |
| 5,288,159 | 2/1994 | Wirt | 401/133 |
| 5,320,845 | 6/1994 | Py | 424/427 |
| 5,337,924 | 8/1994 | Dickie | 222/215 |
| 5,425,480 | 6/1995 | Rabenau et al. | 222/153.07 |

FOREIGN PATENT DOCUMENTS

| | | | |
|---|---|---|---|
| 99706 | 2/1984 | European Pat. Off. | 222/215 |
| 0196288 | 10/1986 | European Pat. Off. | |
| 2694492 | 2/1994 | France | |
| 2278334 | 11/1994 | United Kingdom | 222/215 |
| 9414356 | 7/1994 | WIPO | |

*Primary Examiner*—Andres Kashnikow
*Assistant Examiner*—Philippe Derakshani
*Attorney, Agent, or Firm*—Walter A. Hackler

[57] ABSTRACT

A specific liquid drop volume dispenser includes a container having side walls squeezable in a radial direction to a longitudinal axis of the container in order to dispense liquid drops therefrom at one end of the container. A rigid member is disposed in an operative relationship with the squeezable side walls, for limiting collapse of the squeezable side walls, in order to limit liquid drops dispensed from the container to a specific volume upon a single squeezing of the squeezable side walls, the squeezable side walls having sufficient resiliency to expand, after being squeezed to the rigid member, and draw therebetween, from a remainder of said container, a volume of liquid equal to the dispensed specific volume.

9 Claims, 2 Drawing Sheets

SPECIFIC VOLUME DISPENSER

The present invention generally relates to liquid drop dispensers and is more specifically directed to a liquid drop volume dispenser for providing a predetermined volume of solution.

Many liquid dispensers of the squeeze-bottle type have been developed for dispensing medicinal solutions in droplet form. Most conventional dispensers include a container formed from a resilient plastic material having an opening therein for producing drops of liquid which are dispensed from the container upon squeezing thereof.

Medications are often prescribed which must be dispensed in a metered amount over a predetermined period of time. The medication is typically packaged and marketed in containers enabling individual self-administrable dosages and the user typically self-administers the medication over a predetermined period of time.

This is often the case in the field of ophthalmology wherein various forms of medication are frequently prescribed for the patient to be dispensed in metered drops from a disposable container. Any number of medications may be administered in this manner and such medications typically include decongestants, antibiotics, antinflammatories, antiglaucomic medication, antibacterials, anesthetics, mydriatics, anti-cholinergics, antibiotics as well as combinations thereof.

Since the dispensed drops are to be metered, it is important that a predetermined volume of solution is dispensed per drop, and it is important that only one drop be dispensed per squeeze of the container. Naturally, the dispenser must be suitable for providing multiple doses or drops from a single container, and each of the drops must be of equal size.

Many types of metered valve arrangements have been developed for use in connection with dispensing bottles. However, each of these complicated valve systems are expensive to manufacture.

The present invention provides for a specific liquid volume drop dispenser which provides a specific dosage, namely, one drop of a proper, predetermined volume of solution to be dispensed per squeeze. The container is of sufficient volume to provide multiple doses, and simplicity of construction enables a low manufacturing cost.

SUMMARY OF THE INVENTION

A specific liquid drop volume dispenser, in accordance with the present invention, generally includes a container having side walls squeezable in a radial direction to a longitudinal axis of the container and means, defining an opening in the container, for dispensing liquid drops therefrom at one end of the container.

A rigid member disposed in operative relationship with squeezable side walls is provided for limiting the collapse of the squeezable side walls in order to limit liquid drops dispensed from the container to a specific volume upon a simple squeezing of the squeezable side walls. The squeezable side walls have sufficient resiliency to expand, after being squeezed to the rigid member, and draw therebetween, from a remainder of the container, a volume of liquid equal to the dispensed specific volume. That is, when the container is formed of a suitable material such as polyethylene, there is sufficient memory of the material to expand subsequent to squeezing thereof.

In one embodiment of the present invention, the container includes a forward, generally cylindrical portion and a rearward bulb portion. The means defining an opening is disposed in the cylindrical portion, and the squeezable side walls comprise two sides of the bulb portion. In addition, in this embodiment of the present invention, the rigid member is generally flat and disposed along the longitudinal axis with one of the bulb portion sides protruding on each side of the flat rigid member.

Each of the bulb portion sides is provided with an area significantly smaller than a surface area of a user's thumb, thereby limiting compression of the protruding bulb portions to opposing surfaces of the flat rigid member.

Preferably, the specific liquid volume dispenser is of unitary construction with the container, rigid member and the bulb portion all being formed of a plastic material.

In another embodiment of the present invention, the rigid member is disposed within the container and proximate another end of the container remote from the opening. In this embodiment of the invention, the rigid member is cylindrical and disposed coaxially with the squeezable side walls with a diameter smaller than the container. Thus, the rigid member in this embodiment of the present invention provides an internal stop to limit squeezed side walls to a repeatable position.

Preferably, the rigid member extends from another end of the container to a point past a middle of the container. In this manner, contact is assured between the squeezable walls and the rigid member upon squeezing of the walls.

Preferably, in this embodiment of the present invention, construction is unitary with the rigid member in the squeezable side walls, all being formed from a plastic material with the rigid member having side walls of a thickness significantly greater than the thickness of the container side walls, which are squeezable.

BRIEF DESCRIPTION OF THE DRAWINGS

The advantages and features of the present invention will be better understood by the following description when considered in conjunction with the accompanying drawings in which.

DETAILED DESCRIPTION

Figure 1:
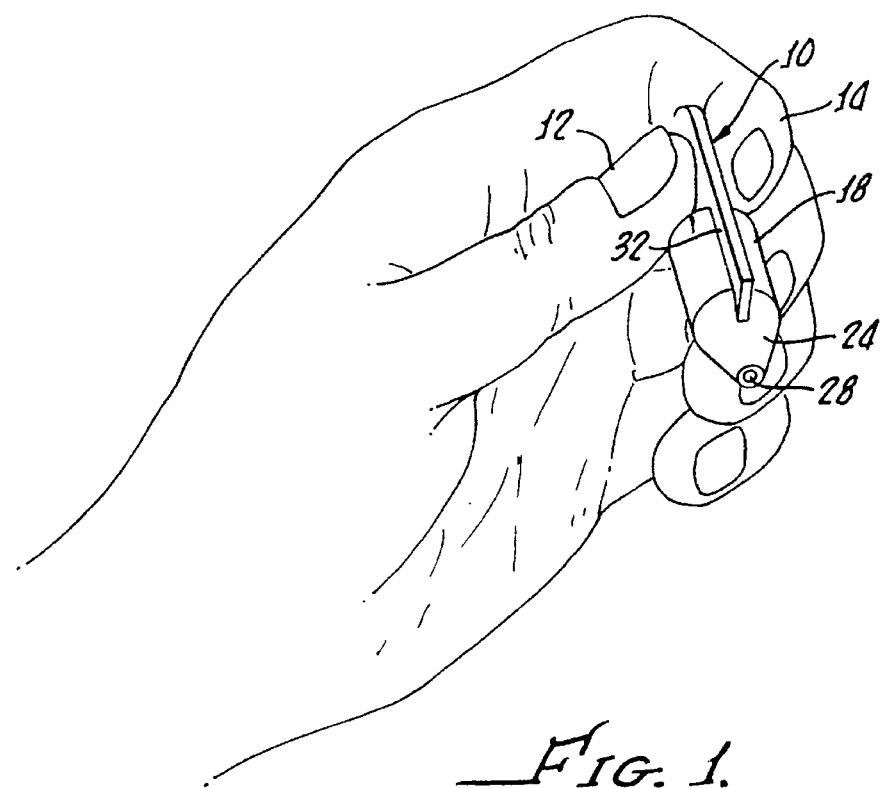
FIG. 1 is a perspective view of one embodiment of the present invention depicting its use by a patient.

Turning now to FIG. 1, there is shown one embodiment 10 of the specific liquid drop volume dispenser in accordance with the present invention shown in operative position with a user's thumb 12 and forefinger 14 for dispensing a single drop of predetermined volume for each squeezing action between the thumb 12 and forefinger 14.

Figure 2:
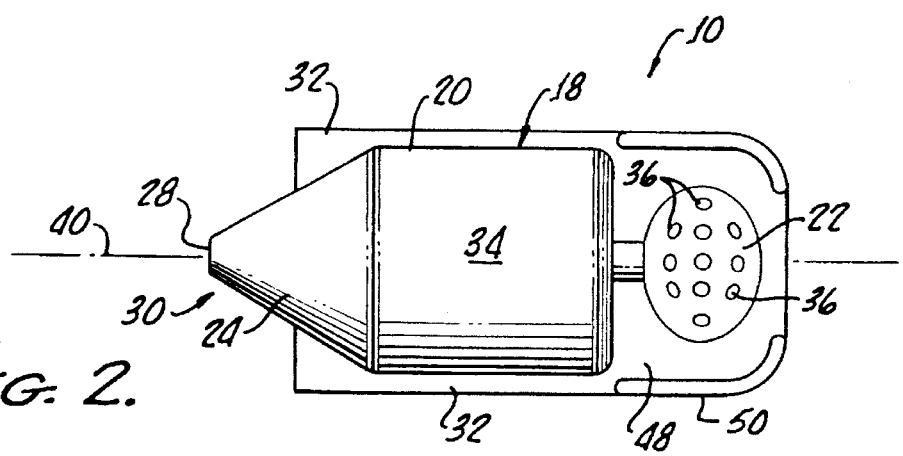
FIG. 2 is a plan view of the invention, generally showing a forward, generally cylindrical portion and a rearward bulb portion.
Figure 3:
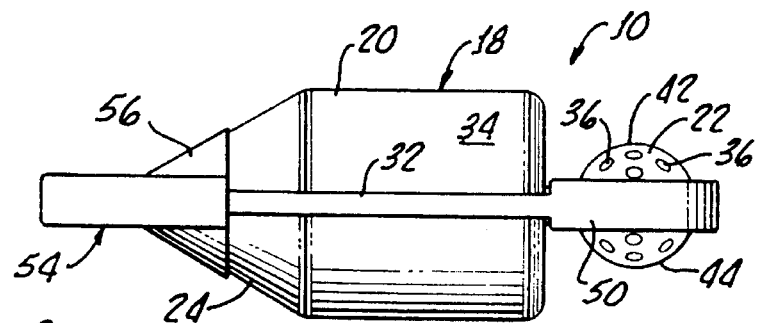
FIG. 3 is a side view of the present invention with a cap disposed in a sealing arrangement with the dispensing opening to facilitate storage of the dispenser between use.

As also shown in FIGS. 2 and 3, the dispenser 10 includes a container 18 having a forward, generally cylindrical portion 20 and a rearward bulb portion 22. A conical nozzle portion 24 extending from the generally cylindrical portion 20 provides a means for defining an opening 28 at one end 30, a dispenser 10 for dispensing liquid drops therefrom.

A rigid member 32, disposed in an operative relationship with the rearward bulb portion 22, as herein-after described in greater detail, provides a means for limiting collapse of the bulb portion 22 in order to limit liquid drops dispensed from the container 18 to a specific volume upon a single squeezing of the bulb 22.

Preferably, the dispenser 10 is of unitary construction with the container 18 having a forward cylindrical portion 20 and a rearward bulb portion 22, as well as the rigid member 32, being formed from a single plastic material such as, for example, polyethylene.

A side wall 34 of the forward cylindrical portion 20 is of sufficient thickness to maintain a fixed volume of solution and is also resistant to deformation. However, the bulb portion 22 is formed with thinner side walls which may include varying thicknesses as indicated by the circles 36 in order to provide a deformable bulb portion 22 with sufficient resiliency to expand, after being squeezed to the rigid member 32, as shown in FIG. 1, in order to draw therebetween from the forward cylindrical portion 20 a volume of liquid equal to the dispensed specific volume drop.

As shown in FIG. 1, the rigid member 20 is generally flat and disposed along a longitudinal axis 40 of the container 20 with bulb portion sides 42, 44 protruding on each side. Importantly, each of the bulb portion sides 42, 44 has an area significantly smaller than the surface area of the user's thumb and forefinger (see FIG. 1), thereby limiting compression of the bulb portion sides 42, 44 to the opposing surfaces 48, 50 of the flat, rigid member 32.

Also shown in FIG. 3 is a cap 54, having a blunt portion 56 for sealing the opening 28 to facilitate storage of the dispenser 10 between uses.

Figure 4:
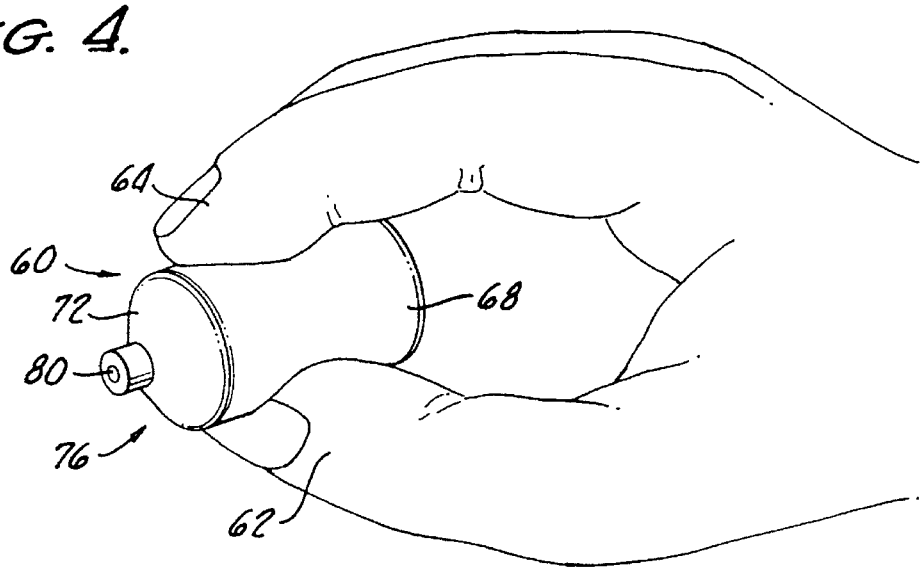
FIG. 4 is a perspective view of another embodiment of the present invention depicted as it may be used by a patient.

Turning now to FIG. 4, there is shown a second embodiment of a specific liquid drop volume dispenser, in accordance with the present invention, as it may be used between a thumb and forefinger of a user for dispensing drops therefrom.

The dispenser 60 generally includes a container 68 having squeezable side walls. A conical nozzle 72 formed in one end 76 of the container 68 provides means defining an opening 80 for dispensing liquid drops therefrom. A rigid member 84 disposed within the container 68 proximate another end 82 of the container 68 and remote from the opening 80 provides a means for limiting collapse of the squeezable side walls 70 in order to limit liquid drops dispensed from the container 68 to a specific volume upon a single squeezing of the squeezable side walls 70.

The dispenser 60 is preferably of unitary construction and formed from a material such as polyethylene. Side walls 86 of the rigid member are of sufficient thickness to prevent deformation whilst side walls 70 are of sufficient thickness enabling squeezing between the thumb 62 and forefinger 64, while at the same time providing resiliency to expand, after being squeezed to the rigid member 84, in order to draw therebetween, from a remainder of the container 68, a volume of liquid equal to the dispensed specific volume. It should be appreciated that the dispenser 60 may be useful for dispensing only a finite number of drops, the total volume of which being less than the volume of the container 68.

Figure 5:
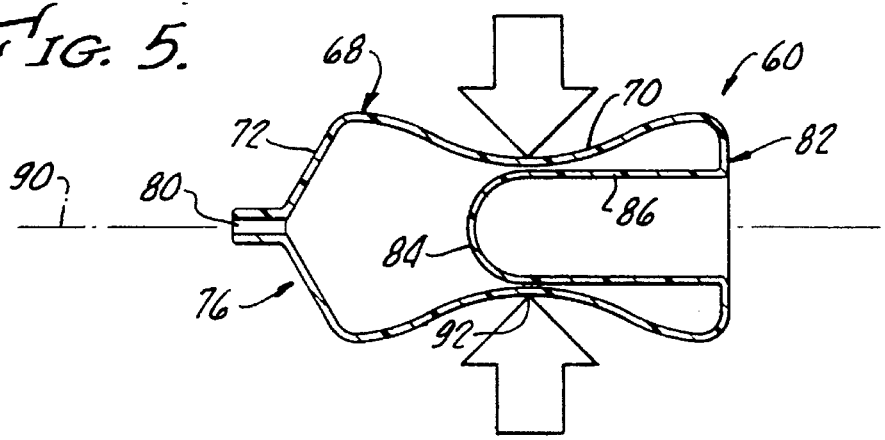
FIG. 5 is a cross-sectional view of the second embodiment of the present invention showing an internally disposed rigid member positioned for limiting the movement of squeezable outer walls.
Figure 6:
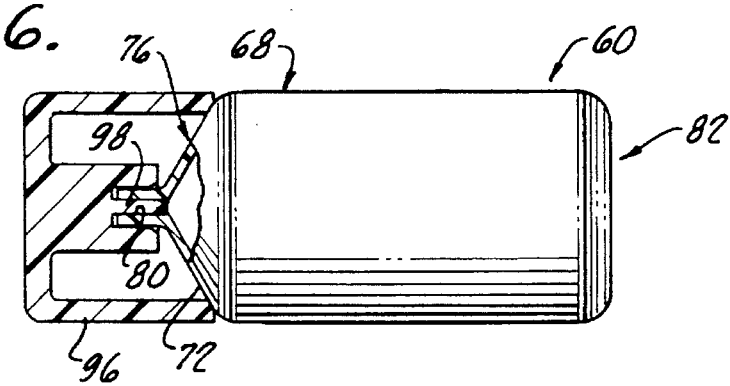
FIG. 6 is a side view of the second embodiment of the present invention with a cap positioned thereon and sealing an opening to facilitate storage thereof.

As shown in FIGS. 5 and 6, the rigid member 84 is disposed coaxially with the squeezable side walls 70 along a longitudinal axis 90 and has a diameter smaller than the container 68. In order to ensure consistent drop size, the rigid member 84 extends from the container end 82 to a point past a middle of a container 68.

As shown in FIG. 6, a cap 96 may be provided which includes a plug 98 for sealing an opening 80 to facilitate storage of the dispenser 60 between uses.

Although there has been hereinabove described a specific liquid drop volume dispenser in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed:

1. A specific liquid drop volume dispenser comprising:

a forward portion having walls resistant to deformation;

a rearward portion, in fluid communication with said forward portion and having side walls squeezable in a radial direction to a longitudinal axis of the forward and rearward portions, and means, defining an opening in said forward portion for dispensing liquid drops therefrom; and rigid member means, disposed in an operative relationship with the squeezable side walls and exterior thereto, for limiting collapse of the squeezable side walls, in order to limit liquid drops dispensed from the container to a specific volume upon a single squeezing of the squeezable side walls, the squeezable side walls having sufficient resiliency to expand, after being squeezed to the rigid member means, and draw therebetween, from the forward portion, a volume of liquid equal to the dispensed specific volume.

2. The specific liquid drop volume dispenser according to claim 1 wherein said rearward portion is in the form of a bulb and said squeezable side walls comprising two sides of the bulb.

3. The specific liquid drop volume dispenser according to claim 2 wherein said rigid member is generally flat and disposed along the longitudinal axis with one of the bulb portion sides protruding on each side of the flat rigid member.

4. The specific liquid drop volume dispenser according to claim 3 wherein each one of the bulb portion sides has an area significantly smaller than a surface area of a user's thumb, thereby limiting compression of the protruding bulb portions to opposing surfaces of the flat rigid member.

5. The specific liquid drop volume dispenser according to claim 4 wherein the dispenser is of unitary construction with the container, rigid member and bulb portion all being formed from a plastic material.

6. A specific liquid drop volume dispenser comprising:

a container having a forward portion, a rearward bulb portion and means, defining an opening in the forward portion, for dispensing liquid drops therefrom, said rearward bulb portion having side walls squeezable in a radial direction to a longitudinal axis of the container; and rigid member means, disposed in an operative relationship with the squeezable side walls and exterior thereto, for limiting collapse of the squeezable side walls in order to limit liquid drops dispensed from the container to a specific volume upon a single squeezing of the squeezable side walls, the squeezable side walls having sufficient resiliency to expand, after being squeezed to the rigid member means, and draw therebetween from the forward portion, a volume of liquid equal to the dispensed specific volume.

7. The specific liquid drop volume dispenser according to claim 6 wherein said rigid member is generally flat and disposed along the longitudinal axis with one of the bulb portion sides protruding on each side of the flat rigid member.

8. The specific liquid drop volume dispenser according to claim 7 wherein each one of the bulb portion sides has an area significantly smaller than a surface area of a user's thumb, thereby limiting compression of the protruding bulb portions to opposing surfaces of the flat rigid member.

9. The specific liquid drop volume dispenser according to claim 8 wherein the dispenser is of unitary construction with the container, rigid member and bulb portion all being formed from a plastic material.

* * * * *